United States Patent [19]

Banks

[11] Patent Number: 5,227,493

[45] Date of Patent: Jul. 13, 1993

[54] FLUORINATED SULFONAMIDE DERIVATIVES

[75] Inventor: Ronald E. Banks, Stockport, England

[73] Assignee: Air Products and Chemicals, Inc., Allentown, Pa.

[21] Appl. No.: 576,291

[22] Filed: Aug. 31, 1990

[51] Int. Cl.$^5$ ........................................... C07D 213/02
[52] U.S. Cl. ................................. 546/307; 546/122; 546/143; 546/159; 546/312; 544/199; 544/210; 544/211; 544/213; 544/237; 544/291; 544/292; 544/293; 544/323; 544/327; 544/332; 544/334; 544/335
[58] Field of Search ............... 546/122, 143, 159, 307, 546/312

[56] References Cited

U.S. PATENT DOCUMENTS

| | | | |
|---|---|---|---|
| 2,519,983 | 8/1950 | Simons | 204/59 R |
| 3,923,810 | 12/1975 | Harrington et al. | 546/312 |
| 4,479,901 | 10/1984 | Barnette | 540/569 |
| 4,828,764 | 5/1989 | DesMarteau | 552/627 |

FOREIGN PATENT DOCUMENTS 3623184 1/1988 Fed. Rep. of Germany.

OTHER PUBLICATIONS

Banks and Khazaei, J. of Fluorine Chemistry vol. 46, pp. 297–305 (1990).

R. E. Banks, et al., "Fluorination of 2-Nitropropane and Malonic Ester with Undecafluoropiperidine," Chem. and Ind., (1964) p. 1864.

R. E. Banks, et al, "N-Fluoro-Compounds. Part IV. Photochemical and Fluoride-initiated Reactions between Perfluoro-N-Fluoropiperidine and Perfluoropropene," J. Chem. Sec., Perkin Transactions I, (1972) p. 1098.

R. E. Banks, et al, "N-Halogeno Compounds. Part 9. N-Fluoroquinuclidinium Fluoride-a New Electrophilic Fluorinating Agent," J. Chem. Soc., Perkin Trans. I, (1988) p. 2805.

R. E. Banks, et al, "Polymeric Analogues of Electrophilic Fluorinating Agents of the N-F Class," J. Fluorine Chem., (1986) 34, p. 281.

S. T. Purrington, et al., "1-Fluoro-2-Pyridone: A Useful Fluorinating Reagent," J. Org. Chem., (1983) 48, p. 761.

S. T. Purrington, et al, "Selective Fluorinations with 1-Fluoro-2-Pyridone," J. Fluorine Chem., (1984), p. 43.

E. Differding, et al., "New Fluorinating Reagents. I. The First Enantioselective Fluorination Reaction," Tetrahedron Lett. (1988) 29, p. 6087.

R. E. Banks, et al, "N-Halogeno-Compounds. Part 10, N-Fluoroquinuclidinium Triflate" J. Fluorine Chemistry, (1988), 41, p. 297.

Primary Examiner—Thurman K. Page
Assistant Examiner—Jyothsna Venkat
Attorney, Agent, or Firm—Russell L. Brewer; James C. Simmons; William F. Marsh

[57] ABSTRACT

N-fluoro perfluoroheterocyclic sulfonamides of the following Formula I

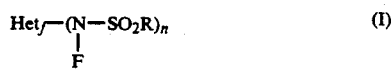

wherein $Het_f$ represents an aromatic perfluoroheterocyclic radical of valency n and each R independently represents a substituted or unsubstituted $C_1$–$C_{30}$ alkyl, $C_6$–$C_{14}$ aryl substituted $C_1$–$C_{10}$ alkyl, $C_6$–$C_{14}$ aryl, or $C_1$–$C_{10}$ alkyl substituted $C_6$–$C_{14}$ aryl group, are novel electrophilic fluorinating agents. Preferably $Het_f$ is a perfluorinated nitrogen-containing aromatic group, especially pyridyl, pyrimidinyl, pyrazinyl or 1,3,5-triazinyl; n is 1; and R is perfluorinated, especially trifluoromethyl.

10 Claims, No Drawings

OTHER PUBLICATIONS

I. V. Vigalok, et al., "Salts of Organic Fluoronitrogen 1-Fluoro-1-Alkyl-2,2,6,6-Tetramethylpiperidinium Cation," J. Org. Chem., USSR, (1983) 19, p. 1203.

T. Umemoto, et al., "N-Fluoropyridinium Triflate and its Analogs, The First Stable 1:1 Salts of Pyridine Nucleus and Halogen Atom," Tetrahedron Letters, vol. 27, (1986), p. 3271.

T. Umemoto et al, "N-Fluoropyridinium Triflate and its Derivatives: Useful Fluorinating Agents," Tetrahedron Letters, vol. 27, (1986), p. 4465.

T. Umemoto, et al., "α-Fluorination of Sulfides with N-Fluoropyridinium Triflates," Bull. Chem. Soc. Jpn., (1986) vol. 59, p. 3625.

S. T. Purrington, et al, "The Application of Elemental Fluorine in Organic Synthesis," Chem. Rev. 1986, 86, p. 997.

G. G. Furin, "Some Electrophilic Fluorination Agents," Eds. L. German and S. Zemskov, Springer-Verlag Berlin, 1986, pp. 35–68.

J. Foropoulos, Jr., et al., "Synthesis, Properties, and Reactions of Bis(Trifluoromethyl)Sulfonyl) Imide, $(CF_3SO_2)_2NH$"; Inorg. Chem. (1984), 23, p. 3720.

R. E. Banks, et al., "Heterocyclic Polyfluoro-Compounds. Part X. Nucleophilic Substitution in Tetrafluoropyrimidine", J. Chem. Soc., Section C, (1967) p. 1822.

FLUORINATED SULFONAMIDE DERIVATIVES

TECHNICAL FIELD OF THE INVENTION

The present invention relates to electrophilic fluorinating agents of the N-F class and provides novel fluorinated sulfonamide derivatives, methods for their preparation, and their use as fluorinating agents.

BACKGROUND OF THE INVENTION

There is a demand for fluorinating agents which are site-selective towards organic, especially carbanionic, substrates, especially for use in the preparation of pharmacologically active compounds. A number of such electrophilic fluorinating agents are known but are limited to their commercial utility in that they are expensive, hazardous, inconvenient to handle, lack stability and/or are insufficiently selective for general use.

Fluorine ($F_2$) solutions in halogenated or other suitable solvents at low temperature (e.g. $-78°$ C.), trifluoromethyl hypofluorite ($CF_3OF$), cesium fluoroxysulfate ($CsSO_4F$) and perchloryl fluoride ($FClO_3$) are all active electrophilic fluorinating agents (S. T. Purrington et al, Chem. Rev. 1986, 86, 997 and G. G. Furin in "New Fluorinating Agents in Organic Synthesis", Ed. L. German and S. Zemskov, Springer-Verlag: Berlin, 1989, 35–68) but are either not sufficiently selective or too hazardous for general use. Xenon difluoride ($XeF_2$) is potentially less hazardous but is too expensive in many applications.

Recently attentiaon has been directed to the use of compounds of the N-F class, i.e. having an N-F bond, as electrophilic fluorinating agents. The prototypical member of this class is perfluoro-N-fluoropiperidine (R. E. Banks and G. E. Williamson, Chem. Ind. (London), 1964, 1864 and R. E. Banks et al, J. Chem. Soc., Perkin Trans. I, 1972, 1098). However, this compound is obtainable only in low yields by electrochemical fluorination of pyridine (about 8% yield) or 2-fluoropyridine (about 13% yield) in anhydrous hydrogen fluoride. Furthermore, it has been found to be inadequately reactive in several applications and, on transfer of fluorine to a carbanionic substrate, liberates the imidoyl fluoride perfluoro-1-azacyclohex-1-ene which then competes for the substrate. Similar problems militate against use of the analogous compounds perfluoro-(N-fluoro-2,6-dimethylpiperidine) and perfluoro-N-fluoromorpholine (R. E. Banks et al, J. Chem. Soc., Perkin Trans. I, 1988, 2805) and of poly[perfluoro-(N-fluoropiperidin-4-ylethylene)] (R. E. Banks & E. Tsiliopoulos, J. Fluorine Chem., 1986, 34, 281) as electrophilic fluorinating agents.

Other members of the N-F class include N-fluoropyridin-2(1H)-one (S. T. Purrington and W. A. Jones, J. Org. Chem. 1983, 43, 761 and J. Fluorine Chem., 1984, 26, 43); N-fluoro-sulfonamides (U.S. Pat. Nos. 4,479,901, 4,828,764 and DE 3623184 A); camphor-derived enantioselective N-fluoro-sultams (E. Differding and R. W. Lang, Tetrahedron Lett., 1988, 29, 6087); N-fluoroquinuclidinium salts (R. E. Banks et al, J. Chem. Soc. Perkin Trans. I, 1988, 2805 and R. E. Banks & I. Sharif, J. Fluorine Chem., 1988 41, 297), N-fluoro-N-alkyl-2,2,6,6,-tetramethyl piperidinium chlorate (I. V. Vigalok et al, J. Org. Chem. USSR, 1983, 19, 1203), and N-fluoropyridinium salts (Umemoto et al, Tetrahedron Lett. 1986, 27, 3271 & 4465 and T. Umemoto & G. Tomizawa, Bull. Chem. Soc. Jpn., 1986, 59, 3625). N-Fluoroquinuclidinium fluoride and triflate and N-fluoro-N-methyl, -propyl or -neopentyl -p-toluene-sulfonamides are available commercially.

U.S. Pat. No. 4,828,764 discloses that certain N-fluoro-N-perfluoroalkyl or perfluoroaryl sulfonamides including, inter alia, those of the formula $R_fSO_2NFR$ are electrophilic fluorinating agents. In said formula $R_f$ represents a perfluorinated $C_1$–$C_{30}$ alkyl, $C_3$–$C_{30}$ cycloalkyl, $C_6$–$C_{14}$ aryl substituted $C_1$–$C_{10}$ alkyl or a $C_6$–$C_{14}$ aryl group and R represents a $C_1$–$C_{30}$ alkyl, $C_3$–$C_{30}$ cycloalkyl, $C_6$–$C_{14}$ aryl substituted $C_1$–$C_{10}$ alkyl, or $C_6$–$C_{14}$ aryl group optionally substituted with one or more inert substituents including, inter alia, fluorine and, when $R_f$ is trifluoromethyl, R alternatively can represent perfluoromethylsulfonamido. The preferred fluorinating agents are stated to be N-fluorobis(trifluoromethanesulfon)imide ($R_f$=$CF_3$ and R=$CF_3SO_2$) and N-fluoro-N-methyl-trifluoromethanesulfonamide ($R_f$=$CF_3$ and R=$CH_3$). The former compound (also known ad DesMarteau Reagent) is a powerful electrophilic fluorinating agent which is capable of fluorinating benzene to fluorobenzene at room temperature, but is tedious to prepare requiring eight or nine reaction steps from readily available material.

SUMMARY OF THE INVENTION

Having regard to the above, it is an object of the present invention to provide an effective electrophilic fluorinating agent which is stable, relatively inexpensive and readily obtainable from presently commercially available starting materials. As explained in further detail below, it has been found that perfluoroheterocyclic N-fluoro-sulfonamides fulfill these requirements.

DETAILED DESCRIPTION OF THE INVENTION

According to a first aspect of the present invention, there is provided novel N-fluoro-perfluoro-heterocyclic sulfonamides of the following Formula I

$$\text{Het}_f\!\!-\!\!\underset{F}{(N\!\!-\!\!SO_2R)_n} \qquad (I)$$

wherein $\text{Het}_f$ represents an aromatic perfluoroheterocyclic radical of valency n and each R independently represents a substituted or unsubstituted $C_1$–$C_{30}$ alkyl, $C_6$–$C_{14}$ aryl substituted $C_1$–$C_{10}$ alkyl, $C_6$–$C_{14}$ aryl, or $C_1$–$C_{10}$ alkyl substituted $C_6$–$C_{14}$ aryl group. Unless otherwise stated or clear from the context, the term "alkyl" used herein includes cycloalkyl.

n is the valency of the perfluoroheterocyclic radical $\text{Het}_f$ and usually is 1, 2 or 3.

As mentioned above, $\text{Het}_f$ is an aromatic perfluoroheterocyclic radical. Preferably $\text{Het}_f$ is a perfluorinated nitrogen containing aromatic group such as pyridazinyl, quinolyl, isoquinolyl, naphthyridinyl, phthalazinyl, cinnolinyl, quinazolinyl, quinoxalinyl or: especially pyridyl, pyrimidinyl, pyrazinyl or 1,3,5-triazinyl. However, $\text{Het}_f$ does not necessarily contain a ring nitrogen atom and can be, for example, perfluorofuryl or perfluorothienyl.

R is hydrocarbyl as defined above, optionally substituted by one or more substituents which are inert in the sense that they do not substantially reduce the effectiveness of the relevant compound as an electrophilic fluorinating agent. Suitable substituents include halogen, alkoxy, cyano, nitro, ester, ketol, alkyl sulfonyl, sulfonyl fluoride, dialkylamino and amido. Presently preferred substituents are chlorine and fluorine and it is particularly preferred that the hydrocarbyl moiety is perfluorinated.

The alkyl groups represented by R can be branched or straight chain groups and it is preferred that such groups have 1 to 8, especially 1 to 4 carbon atoms. atoms. R also can be a cycloalkyl group containing mono- or bi-cyclic aliphatic hydrocarbyl rings, preferably containing 3 to 12, especially 4 to 9, ring carbon atoms.

As mentioned above, R also can be $C_{1-10}$ alkyl 1 substituted $C_{6-14}$ aryl, $C_{6-14}$ aryl or $C_6$–$C_{14}$ aryl substituted $C_{1-10}$ alkyl. When said group contains alkyl, said alkyl usually will be straight or branched chain, preferably having 1 to 8, especially 1 to 4, carbon atoms. The aryl group can be di- or poly-cyclic but preferably is monocyclic, i.e. phenyl, and can be substituted by one or more $C_{1-10}$ alkyl groups.

The presently preferred perfluoroheterocyclic N-fluoro compounds of the invention include:
perfluoro[N-fluoro-N-(4-pyridyl)methanesulfonamide];
perfluoro[N-fluoro-N-(4-pyrimidinyl)methanesulfonamide];
perfluoro[N-fluoro-N-(2-pyrazinyl)methanesulfonamide];
2,4,6-tris-[N-fluorotrifluoromethanesulfonamido]-1,3,5-triazine; and
perfluoro[4,6-bis(N-fluoromethanesulfonamido)pyrimidine].

The perfluoroheterocyclic N-fluoro sulfonamides of Formula I can be prepared by fluorinating a salt, preferably an alkali metal, especially sodium, salt, of the corresponding perfluoroheterocyclic sulfonamide of the following Formula II

wherein n, $Het_f$ and R are as defined above. Suitably, the salts are obtained by treatment of a perfluorinated heterocycle of the formula $Het_fF_n$ (where $Het_f$ and n are as defined above) with the appropriate salt of a sulfonamide of the formula $H_2NSO_2R$ (where R is as defined above).

Suitably, the fluorination is carried out in manner known per se using a stirred-tank batch reactor into which the fluorine is admitted either as a single charge of the gas at sub-atmospheric pressure or as a continuous flow of fluorine blended with nitrogen or other insert diluent at about atmospheric pressure. In the first of said fluorination methods, fluorine is passed into a stirred low temperature solution or suspension of the perfluoroheterocyclic sulfonamide salt in a suitable organic solvent, especially trichlorofluoromethane or acetonitrile (see, for example, R. E. Banks et al, J. Chem. Soc. Perkin Trans. I, 1988, 2805). Usually, the temperature is in the range −35° C. to −78° C. and the fluorine pressure is below about 20 mm Hg (2.7 kPa). In the second method, fluorine heavily diluted with an inert gas, usually nitrogen, is passed through said solution at about ambient pressure (see, for example, U.S. Pat. No. 4,479,901).

At least some of the perfluoroheterocyclic sulfonamides (II) and salts thereof are novel compounds.

The novel fluorinating agents of Formula I are used in manner know per se as electrophilic fluorinating agents (see, for example, R. E. Banks et al J. Chem. Soc. Perkin Trans. I, 1988, 2805).

The invention is illustrated by the following non-limiting Examples.

EXAMPLE I

Perfluoro-[N-fluoro-N-(4-pyridyl)methanesulfonamide]

1) Starting Materials

Commercial pentafluoropyridine was used as received. Trifluoromethanesulfonamide was prepared on a 50 g scale from trifluoromethanesulfonyl fluoride and ammonia according to the method of J. Foropoulos and D. D. DesMarteau (Inorg. Chem., 1984, 23 3720), the yield being 75% [after purification by sublimation (twice)]. The trifluoromethanesulfonyl fluoride was prepared from commercial methanesulfonyl chloride (Lancaster Synthesis) via halogen-exchange with potassium hydrogen difluoride and subsequent electrochemical fluorination (Simons Process) of the methanesulfonyl fluoride thus obtained in a 50 liter cell of classical design (U.S. Pat. No. 2,519,983); the overall yield was 70%.

2) Sodium Salt of Perfluoro-[N-(4-pyridyl)methanesulfonamide]

The sodium salt of trifluoromethanesulfonamide was prepared in 92% yield according to the method of J. Foropoulos and D. D. DesMarteau (supra) ($CF_3SO_2NH_2$ and MeONa in MeOH) except that toluene not benzene was used to wash the resulting solid. A mixture of this salt (8.65 g, 50.6 mmol), pentafluoropyridine (4.20 g, 24.8 mmol), and dry tetrahydrofuran (THF) (50 cm$^3$), sealed in an evacuated Pyrex (Trade Mark) ampoule (150 cm$^3$) fitted with a PTFE-glass valve, was shaken mechanically at 80° C. for 24 hours in an explosion-proof cabinet. The product was diluted with dry diethyl ether (50 cm$^3$) the filtered to remove sodium fluoride. Evaporation of the filtrate followed by sublimation of the solid residue at 30° C. in vacuo to remove trifluoromethanesulfonamide (3.80 g) (identified $^1$H and $^{19}$F n.m.r. and i.r. analysis) provided the sodium salt of perfluoro-[N-(4-pyridyl)methanesulfonamide] (7.10 g, 22.2 mmol, 89.5%) (Found: C, 22.6; H, <0.1; F, 41.6; N, 8.6; S, 10.0%. $C_6F_7N_2NaO_2S$ requires C, 22.5; H, 0.0; F, 41.6; N, 8.3; S, 10.0%), m.p. 285° C., $\delta_F$ [ext. TFA; soln. in $(CD_3)_2CO$] −1.3 (t, 3 Hz; $CF_3SO_2$), −19.7 (complex; 2-, 6-F), −75.9 (complex; 3-, 5-F) p.p.m. (rel. int. 3:2:2). Treatment of a sample (2.00 g, 6.25 mmol) of this salt with 10% aqueous sulfuric acid (30 cm$^3$), followed by continuous ether extraction ($Et_2O$) of the resultant solution, evaporation of the dried ($MgSO_4$) extract, and sublimation of the residue at 60° C., in vacuo, provided perfluoro[N-(4-pyridyl)methanesulfonamide] (0.95 g, 3.19 mmol, 51%) (Found: C, 24.1; H, 0.3; F, 44.8; N, 9.3; S, 10.3%. $C_6HF_7N_2O_2S$ requires C, 24.2; H, 0.3; F, 44.6; N, 9.4; S, 10.0%), m.p. 69°–70° C., $\delta_F$ (ext. TFA; soln. in $CDCl_3$)+3.0 (t, 7.2 Hz; $CF_3SO_2$), −7.9 (complex, 2-, 6-F), −67.1 (complex, 3-, 5-F) p.p.m. (rel. int. 3:2:2), $\delta_H$ [soln. in $(CD_3)_2CO$] 7.45 (br.s; NH) p.p.m.

3) Perfluoro-[N-fluoro-N-(4-pyridyl)methanesulfonamide]

A 200-cm$^3$ fluorination reactor (R. E. Banks et al, J. Chem. Soc., Perkin Trans. I, 1988, 2805) was charged with a solution of the sodium derivative of perfluoro[N-(4-pyridyl)methanesulfonamide] (2.0 g, 6.25 mmol) in dry acetonitrile (200 cm$^3$; distilled off P$_2$O$_5$) containing 5A molecular sieve (0.1 g). The solution was cooled (−30° to −35° C.) and the contents degassed before fluorine was admitted to the evacuated reactor to a pressure of 10 mm Hg (1.3 kPa). Consumption of the halogen began immediately, and more fluorine was admitted periodically from a calibrated stainless steel reservoir to maintain the pressure in the range 10 to 15 mm Hg (1.3 to 2.0 kPa). After 6 hours, during which time the reaction mixture became noticeably yellow, uptake of fluorine appeared to cease. The non-volatile product, plus material obtained by washing out the reactor with dry acetonitrile, was filtered to remove sodium fluoride and spent molecular sieve, then evaporated in vacuo at ambient temperature. The semi-solid pale-yellow residue (1.5 g) was shown by i.r. and n.m.r. spectroscopy to be perfluoro-[N-fluoro-N-(4-pyridyl)-methanesulfonamide] contaminated with perfluoro[N-(4-pyridyl)methanesulfonamide]; the ratio of N-F compound to N-H compound was 10:1 by $^{19}$F n.m.r. analysis, and 9.8:1.0 by standard iodimetric estimation (R. E. Banks and E. D. Burling, J. Chem. Soc., (1965) 6077) of the fluorine attached to nitrogen in a sample (0.320 g) of the mixture. Evaporation of the recovered acetonitrile at ambient temperature and about 10 mm Hg (1.3 kPa) pressure provided more N-F compound [0.44 g; total yield after allowing for the presence of N-H compound (0.56 mmol)=5.52 mmol, (89%)] still contaminated with approximately 9 mole-% of the N-H compound according to $^{19}$F n.m.r. spectroscopy, and possessing the following elemental analysis: Found: C, 23.0; H, 0.2; F, 47.7; N, 8.8; S, 9.8%. Calc. for C$_6$F$_8$N$_2$O$_2$S: C, 22.7; H, 0.0: F, 48.1; N, 8.8; S, 10.1%. The $^{19}$F n.m.r. spectrum of the mixture dissolved in CDCl$_3$ showed absorptions for the N-F compound at −24.5 (m; NF) and −73.5 (m; CF$_3$SO$_2$) (both measured relative to ext. CFCl$_3$), and −6.3 (complex; 2-, 6-F) and −61.2 (complex; 3-,5-F) (both relative to ext. CF$_3$CO$_2$H) p.p.m. (rel. int. 1:3:2:2).

EXAMPLE 2

Fluorination of diethyl phenylmalonate

A solution of diethyl sodio(phenyl)malonate in anhydrous THF [prepared in conventional fashion by adding a 60% dispersion of NaH (0.64 mmol) in oil to PhCH(CO$_2$Et)$_2$ (0.15 g, 0.635 mmol) dissolved in THF (10 cm$^3$)] was added dropwise to a cold (−10° C.) THF solution (15 cm$^3$) of a 9:1 molar mixture (from the experiment described immediately above) of perfluoro-[N-fluoro-N-(4-pyridyl)methanesulfonamide] and its N-H precursor containing 0.20 g (0.63 mmol) of the N-F compound. The reaction mixture was allowed to warm to room temperature, then worked-up as described by R. E. Banks et al (J. Chem. Soc., Perkin Trans I, 1988 2805) for the product from the fluorination of diethyl sodio(phenyl)malonate with N-fluoroquinuclidinium fluoride, to provide diethyl fluoro(phenyl)malonate (0.15 g, 0.59 mmol, 93%) as a colourless oil [Found: C, 61.5; H, 6.2%; M (mass spec.) 254. Calc. for C$_{13}$H$_{15}$FO$_4$: C, 61.4; H, 5.9%; M, 254] with correct spectroscopic properties (i.r.; $^1$H and $^{19}$F n.m.r.).

EXAMPLE 3

Fluorination of benzene

An excess of benzene (0.262 g, 3.36 mmol) and hexafluorobenzene (as an internal $^{19}$F n.m.r. standard) were added by microsyringe to perfluoro-[N-fluoro-N-(4-pyridyl)methanesulfonamide] [0.040 g, 0.126 mmol; 0.014 mmol of the N-H analogue was present too] dissolved in CDCl$_3$ and contained in a 5 mm (o.d.) n.m.r. tube. The mixture was frozen (−196° C.) and de-gassed (3 freeze-pump-thaw cycles) before the tube was sealed in vacuo, allowed to warm to room temperature, and the contents (a homogeneous, colourless solution) subjected to n.m.r. analysis (probe temp. 35° C.). No reaction appeared to have occurred, so the n.m.r. tube was warmed to 60° C. (water bath), kept at that temperature for 10 minutes (the contents became yellow), allowed to cool to room temperature then returned to the n.m.r. spectrometer. The $^{19}$F n.m.r. spectrum obtained revealed that complete conversion of the N-F compound to perfluoro[N-fluoro-N-(4-pyridyl)methanesulfonamide] had occurred, with the associative formation of fluorobenzene in 88% yield.

EXAMPLE 4

Fluorination of anisole

Example 3 above was repeated, using anisole (methoxybenzene; 0.060 g, 0.555 mmol), hexafluorobenzene (0.01 g, 0.054 mmol) and a 9:1 molar mixture (0.024 g) of perfluoro-[N-fluoro-N-(4-pyridyl)methanesulfonamide] (0.076 mmol) and its N-H analogue in deuteriochloroform. N.m.r. analysis of the reaction mixture (after the sealed tube had warmed to room temperature and then been shaken manually for 10 minutes) revealed that the N-fluoro compound had been consumed completely, causing the formation of a 3:1 mixture of o- and p-fluoroanisole in 98% yield.

Perfluoro-[N-fluoro-N-(4-pyridyl)methanesulfonamide] appears to be about as powerful an electrophilic fluorinating agent as the DesMarteau Reagent (CF$_3$SO$_2$)$_2$NF, which effects the halogenation of C$_6$H$_6$ to C$_6$H$_5$F in 100% yield based on 50% completion of reaction during 18 hours at 22° C. (benzene was used in excess). Additionally, not only does synthesis of this new reagent from commercial methanesulphonyl chloride require six steps compared with nine in the case of (CF$_3$SO$_2$)$_2$NF, but the fluorination procedure used here to construct the required N-F bond is both more convenient and potentially less hazardous than that described so far for effecting the conversion of (CF$_3$SO$_2$)$_2$NH to (CF$_3$SO$_2$)$_2$NF. The synthesis of (CF$_3$SO$_2$)$_2$NF could be shortened to eight stages (from CH$_3$SO$_2$Cl) if treatment of the sodium salt (CF$_3$SO$_2$)$_2$NNa to give the N-F compound's immediate precursor, (CF$_3$SO$_2$)$_2$NH] with fluorine proved to proceed smoothly, as in the analogous reaction described in Example 1 above.

EXAMPLE 5

Perfluoro-[N-fluoro-N-(4-pyrimidinyl)methanesulfonamide]

1) Sodium salt of perfluoro-[N-(4-pyrimidinyl)methanesulfonamide]

A mixture of the sodium salt of trifluoromethanesulphonamide (3.38 g, 19.8 mmol), tetrafluoropyrimidine (1.50 g, 9.9 mmol), and dry tetrahydrofuran (50 cm$^3$) contained in a sealed, evacuated, Pyrex (Trade Mark) tube (250 cm$^3$) was stirred magnetically at 50° C. for 24 hours. The product was filtered to remove sodium fluoride, and the filtrate evaporated. Trifluoromethanesulphonamide was removed from the residue by reduced-pressure sublimation, leaving behind the white sodium salt of perfluoro-[N-(4-pyrimidinyl)methanesulphonamide](2.56 g, 8.45 mmol, 85%) (Found: C, 197.7;

H, 0.1; N, 13.8; S, 10.4%. $C_5F_6N_3NaO_2S$ requires C, 19.8; H, 0.0; N, 13.9; S, 10.6%), $\delta_F$ (D$_2$O soln.; ext. CF$_3$CO$_2$H) 28.5 (m; 2-F), 1.2 (s; CF$_3$SO$_2$), −6.2 (m; 6-F), and −91.5 (m; 5-F) p.p.m.

The tetrafluoropyrimidine was prepared from commercial tetrachloropyrimidine by a halogen-exchange reaction, as described by R. E. Banks et al (J. Chem. Soc. (C), 1967, 1822).

2) Perfluoro-[N-fluoro-N-(4-pyrimidinyl)methanesulfonamide]

A cold (−35° C.), efficiently stirred solution of the sodium salt of perfluoro-[N-(4-pyrimidinyl)methanesulphonamide] (1.22 g) in dry acetonitrile (200 cm$^3$) was treated with neat fluorine at 10–15 mmHg (1.3 to 2.0 kPa) pressure until uptake of the halogen appeared to cease (this took nearly 3 hours). The product solution was filtered (to remove sodium fluoride) and the filtrate evaporated, leaving a colourless oily sample (about 1 g) of perfluoro-[N-fluoro-N-(4-pyrimidinyl)methanesulphonamide], shown by $^{19}$F n.m.r. spectroscopy to be contaminated with perfluoro-[N-(4-pyrimidinyl)methanesulphonamide] and its sodium salt. This impure product showed NF absorption at 47.5 p.p.m. in its $^{19}$F n.m.r. spectrum [solution in CH$_3$CN; external CF$_3$CO$_2$H reference (computed chemical shift relative to CFCl$_3$=−29.05 p.p.m.)], and rapidly liberated iodine from aqueous potassium iodide solution. Examination of the filtered iodimetric test solution by $^{19}$F n.m.r. spectroscopy revealed only absorptions assignable to perfluoro-[N-(4-pyrimidinyl)methanesulphonamide] [$\delta_F$ 30.1 (m; 2-F), 2.0 (s; CF$_3$SO$_2$), −0.8 (m; 6-F), and −88.2 (m; 5-F) p.p.m. (CF$_3$CO$_2$H ext. ref)]. Examination by $^{19}$F n.m.r. spectroscopy of the solution prepared by addition of an excess of heat anisole to the impure perfluoro-[N-fluoro-N-(4-pyrimidinyl)methanesulphonamide] revealed the rapid formation at room temperature of an about 1:1 mixture of o- and p-fluoroanisole, accompanied by complete consumption of the N-fluoro-compound.

I claim:

1. An N-fluoro perfluoroheterocyclic sulfonamide of the following formula:

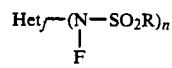

wherein Het$_f$ represents an aromatic perfluoroheterocyclic radical of valency n selected from the group consisting of pyridyl, naphthyridinyl, quinolyl, and isoquinolyl and each R independently represents a C$_1$-C$_{30}$ alkyl, C$_3$-C$_{30}$ cycloalkyl, C$_6$-C$_{14}$ aryl substituted C$_1$-C$_{10}$ alkyl, C$_6$-C$_{14}$ aryl, or C$_1$-C$_{10}$ alkyl substituted C$_6$-C$_{14}$ aryl group, and n is 1, 2 or 3, wherein R may contain one or more substituents selected from the group consisting of halogen, alkoxy, cyano, nitro, ester, ketol, alkyl sulfonyl, sulfonyl fluoride, dialkylamino and amido.

2. The compound of claim 1, wherein R is C$_1$-C$_4$ alkyl, C$_3$-C$_9$ cycloalkyl, phenyl, phenyl-substituted C$_1$-C$_4$ alkyl or C$_1$-C$_4$-substituted phenyl.

3. The compound of claim 2, wherein R represents methyl.

4. The compound of claim 1, wherein R is substituted by one or more chlorine or fluorine atoms.

5. The compound of claim 4, wherein R is perfluorinated.

6. The compound of claim 1, wherein R is trifluoromethyl.

7. The compound of claim 1, wherein n is 1.

8. A compound of claim 7, and 2,4,6-tris wherein Het$_f$ is 4-pyridyl and R is methyl.

9. An N-fluoro perfluoroheterocyclic sulfonamide of the following Formula:

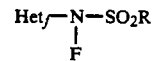

wherein Het$_f$ is an aromatic perfluoroheterocyclic selected from the group consisting of quinolyl, and isoquinolyl.

10. An N-fluoro perfluoroheterocyclic sulfonamide of the following Formula:

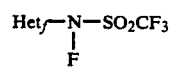

wherein Het$_f$ is pyridyl.

* * * * *